US005484952A

United States Patent [19]
Nolan et al.

[11] Patent Number: 5,484,952
[45] Date of Patent: Jan. 16, 1996

[54] PROCESS FOR THE MANUFACTURE OF ALKYL KETENE DIMER

[75] Inventors: Timothy F. Nolan, New Castle, Del.; Brian M. Stubbs, Sidcup, England

[73] Assignee: Hercules Incorporated, Wilmington, Del.

[21] Appl. No.: 238,293

[22] Filed: May 5, 1994

[30] Foreign Application Priority Data

May 10, 1993 [GB] United Kingdom .................. 9309604

[51] Int. Cl.$^6$ .................................................. C07D 305/12
[52] U.S. Cl. ........................................................... 549/329
[58] Field of Search ............................................ 549/329

[56] References Cited

U.S. PATENT DOCUMENTS

| | | | |
|---|---|---|---|
| 2,238,826 | 4/1941 | Sauer | 549/329 |
| 2,369,919 | 2/1945 | Sauer | 260/550 |
| 3,362,965 | 1/1968 | Englund et al. | 547/329 |
| 3,795,685 | 3/1974 | Sianesi | 260/345.2 |
| 5,252,754 | 10/1993 | Battorff | 549/329 |
| 5,344,943 | 9/1994 | Broland | 549/329 |

FOREIGN PATENT DOCUMENTS

| | | | |
|---|---|---|---|
| 612739 | 1/1994 | European Pat. Off. | 549/329 |
| 2927118 | 1/1981 | Germany | C07C 49/88 |
| 63-258865 | 10/1963 | Japan | C07D 305/12 |
| 63-264545 | 11/1963 | Japan | C07C 49/88 |
| 63-264544 | 11/1963 | Japan | C07C 49/88 |
| 681302 | 2/1993 | Switzerland | 549/329 |
| 94/19306 | 9/1994 | WIPO | 549/329 |

OTHER PUBLICATIONS

Chemical Abstracts, vol. 117, No. 1, Jul. 6, 1992, Columbus, Ohio, USA Nippon Oil and Fats Co., "Preparation of ultra-pure alkylketene dimers" p. 787, column 2, No. 7 788f; & Jpn. Kokai Tokkyo Koho JP-A-O-436 258 (93 36 258).
Chemical Abstracts, vol. 119, No. 13, Sep. 27, 1993, Columbus, Ohio, USA Korea Institute of Science and Technology, "Method for Manufacture of diketene"p. 859, column 2, No. 139 057t; & Jpn. Kokai Tokkyo Koho JP-A-A-05-59 034 (93 59 034).
U.S. Serial No. 08/037,203, filed Mar. 26, 1993 to J. J. Zhang re Process for the Manf. of Alkyl Ketene Dimers by Dimerization with Tertiary Amines.
U.S. Serial No. 08/217,590, filed Mar. 24, 1994 to J. J. Zhang re Process for the Manf. of Alkyl Ketene Dimers by Dimerizaiton with Tertiary Amines.
Derwent Abstract of JP 63258471 A to Nippon Oils & Fats KK re Alkyl–Ketene Dimer Prep. From Fatty Acid Halide and Recovered Lower Tert. Amine Dehydrated Using Ketene Dimer (Oct. 1988).
Derwent Abs. of Russian 1035024–A to Ostrovskii MK re Prepn. of Higher Alkyl–Ketene Dimers By Reacting Mixture of Synthetic Fatty Acids Chloro Anhydride(s) with Tert–Amine, (Aug. 1983).
Derwent Abs. of German 2327988 to Henkel & Cie GmbH re Long–Chain Alkyl–Ketene Dimers Prodn. From Fatty Acid Chloride and Tert Amine, and Purification by Washing, (Jan. 1975).
Sauer, J. C., *Ketene Dimers from Acid Halides*, Journal of the American Chemical Society, 69, pp. 2444–2448 (1947).
Hansen, C. M., "The Three Dimensional Solubility Parameter–Key to Paint Component Affinities: I. Solvents, Plasticizers, Polymers, and Resins", Journal Paint Technology, 39, 104, 1967.
Hansen, C. M., "The Three Dimensional Solubility Parameter–Key to Paint Component Affinities: II and III, II. Dyes, Emulsifiers, Mutual Solubility an Compatibility, & Pigments", Jour. Paint Tech., 39,505, 1967.
Hansen, C. M., "The Universality of the Solubility Parameter", I & EC Product Research and Development, vol. 8, No. 1, Mar., 1969, pp. 2–11.
Derwent Abs. of DT 2335488 to BASF AG re Fatty Alkyl Diketene Prepn. From Fatty Acid Halides and Tertiary Amines and Separation After Adding Carboxylic Acids, and (Feb. 1975).
Derwent Abs. of DE 3434212–A to Schill & Seilacher re Ketene Dimer Prodn. From Fatty Acid Halide and Tert. Amine in Molten Wax With Acid Hyrdolysis, Giving Organic Phase Useful As Or In Paper Size, (Mar. 1986).
Chemical Abstracts, vol. 117, No. 1, Jul. 6, 1992, Columbus, Ohio, USA Nippon Oil and Fats Co., "Preparation of ultra-pure alkylketene dimers" p. 787, column 2, No. 7 788f; & Jpn. Kokai Tokkyo Koho Jp-A-O–436 258 (93 36 258).
Chemical Abstracts, vol. 119, No. 13, Sep. 27, 1993, Columbus, Ohio, USA Korea Institute of Science and Technology, "Method for Manufacture of diketene" p. 859, column 2, No. 139 057t; & Jpn. Kokai Tokkyo Koho JP-A-A-05-59 034 (93 59 034).

*Primary Examiner*—James H. Reamer
*Attorney, Agent, or Firm*—Roy V. Jackson; Mark D. Kuller

[57] ABSTRACT

A process for making an alkyl ketene dimer by the dehydrohalogenation reaction of a $C_8$–$C_{32}$ aliphatic fatty acid chloride with a tertiary amine in an inert solvent and the product of the process; the solvent comprising at an oxygenated hydrocarbon.

61 Claims, No Drawings

PROCESS FOR THE MANUFACTURE OF ALKYL KETENE DIMER

This invention relates to alkyl ketene dimers and processes for making them by the dehydrohalogenation reaction of $C_8$–$C_{32}$ fatty acid halides with tertiary amines in inert solvents.

BACKGROUND OF THE INVENTION

The reaction of fatty acid chlorides with tertiary amines in a variety of inert solvents to make alkyl ketene dimers, which are useful as constituents of paper sizes as well as for other applications in industry, is well known, for instance from U.S. Pat. No. 2,238,826 and an article by J. C. Sauer, *Ketene Dimers from Acid Halides*, in the Journal of the American Chemical Society, 69 2444–8 (1947).

That reaction in the inert solvent produces alkyl ketene dimer (AKD) in solution and tertiary amine hydrochloride as a finely divided precipitate. Conventionally, the precipitate is separated from the dimerization slurry by liquid/liquid aqueous extraction of the amine hydrochloride salt. The filtrate containing the alkyl ketene dimer and excess tertiary amine is then stripped of solvent under reduced pressure using a rotary evaporator and a water bath at about 80° C. to give the alkyl ketene dimer. The product typically has an alkyl ketene dimer assay of 83% or higher and a non-volatile content up to 99.8%.

Among the solvents conventionally used are benzene, toluene, xylene, ligroin, chlorobenzene, dichlorobenzene, diethyl ether, dibutyl ether, chloroform, carbon tetrachloride, and trichloroethylene. They can be classified as:

1. alkanes and alkane petroleum fractions;
2. aromatic hydrocarbons such as benzene, toluene, and xylene;
3. chlorinated solvents such as chlorobenzene, dichlorobenzene, chloroform, carbon tetrachloride, propylene dichloride, and trichloroethylene; and
4. ethers such as diethyl ether, diisopropyl ether, diisoamyl ether, and di-n hexyl ether.

The conventional dimerization solvents typically used in current industrial applications are either unacceptably toxic, particularly benzene and toluene, or are potentially environmentally objectionable, including the whole class of the chlorinated solvents. Thus the need exists for an alkyl ketene dimerization process that uses a solvent with less potential for health and environmental problems than aromatic hydrocarbons or halogenated solvents.

However, in some of the known solvents the alkyl ketene dimerization reaction can produce a low yield of AKD (for instance, below 80%), an excessively viscous dimerization mixture, or very small amine-hydrohalide crystals in the dimerization slurry. If the dimerization reaction slurry is either highly viscous or contains amine-hydrohalide crystals that are very small, separation of the tertiary amine hydrochloride precipitate from the reaction mixture can be extremely difficult.

Also, the conventional separation of salt precipitate from the dimerization slurry, involving liquid/liquid aqueous extraction of the salt, introduces moisture that is likely to cause hydrolysis of the alkyl ketene dimer and lessen the yield of the product (or to use the more accurate term, the "assay", which refers specifically to the yield of pure product in the gross amount produced).

Because the extraction method reduces the AKD assay, it is desirable to produce the amine-hydrohalide precipitates in such a way that they can readily be separated by such mechanical methods as filtration, sedimentation and decantation, possibly after centrifugation, or a combination of centrifugation and filtration, while at the same time avoiding health and environmental problems.

SUMMARY OF THE INVENTION

The invention comprises a process for making an alkyl ketene dimer by the dehydrohalogenation reaction of a $C_8$–$C_{32}$ aliphatic fatty acid halide, preferably a chloride, with a tertiary amine in a solvent that is not reactive with the ingredients of the reaction mixture, herein referred to as an inert solvent, the solvent comprising at least about 30% of an oxygenated hydrocarbon or mixture of oxygenated hydrocarbons, preferably having a melting point below 25° C. and boiling point above 70° C. Preferably, the process produces amine-hydrohalide crystals that are large enough to be readily separated using mechanical techniques and an assay of alkyl ketene dimer in solution of over 80%. Oxygenated hydrocarbons are hydrocarbons in which the molecule combines one or more oxygen atoms with the carbon and hydrogen atoms, the preferred compounds being ketones, esters, and aromatic ethers. The invention is also directed to the resultant alkyl ketene dimer.

To achieve these results, the solvent must have sufficient polarity to produce the said high assay of alkyl ketene dimer without being so polar that the assay is reduced by excessive moisture (herein referred to as moderate polarity and hydrogen bonding capabilities). Preferably, the reaction is carried out by reacting a $C_8$–$C_{22}$ saturated linear fatty acid chloride with a linear tertiary amine.

Preferably, the moderate polarity and hydrogen bonding capabilities required for acceptable solvents according to the invention are determined by using a solubility parameter scale developed by Hansen. The original solubility parameter concept was formulated by Hildebrand, where the total solubility parameter ($\delta_T$) is related to the liquid cohesive forces. As described in "The Three dimensional Solubility Parameter—key to Paint Component Affinities: I", Journal of Paint Technology 39 (February 1967), Hansen divided the total solubility parameter into dispersive ($\delta_D$), polar ($\delta_P$) and hydrogen bonding ($\delta_H$) parameters. See also "The Universality of the Solubility Parameter" *I & E.C. Product Research and Development* 8 (March 1969). (The disclosures of those two articles are incorporated herein by reference). Solvents can be placed into two or three dimensional maps in which the axes of the maps are the dispersive, polar and hydrogen bonding solubility parameters. On a two dimensional graph in which the x-y axes are the Hansen polar and hydrogen bonding solubility parameter scales respectively, the x and y coordinates of available hydrocarbon solvents for AKD can be shown.

According to a preferred embodiment of the invention particularly suitable for processes involving mechanical separation, the polar and hydrogen bonding solubility parameters of the oxygenated hydrocarbon solvent have Hansen polar (abscissa, x) and hydrogen bonding (ordinate, y) solubility values lying on or within a solubility parameter circle drawn on a parameter solubility map where the x-y axes are the Hansen polar and hydrogen bonding solubility parameter scales in $MPa^{1/2}$ units, respectively, the circle radius being 3.5 $MPa^{1/2}$, and the center of the circle the center having 6.25 and 4 as its x, y coordinates, the oxygenated hydrocarbon solvents having x, y coordinates such that $x^2+y^2-12.5x-8y+55.0625 \leq 12.25$.

According to another preferred embodiment particularly suitable for processes involving mechanical separation, the center of the circle has 6 and 4 as its x, y coordinates such that $x^2+y^2-12x-8y+52 \leq 12.25$, provided that the Hansen polar solubility value of the oxyenated hydrocarbon solvent is greater than 2.75 MPa$^{1/2}$.

According to the invention, the polar and hydrogen bonding solubility parameters of preferred oxygenated hydrocarbon solvents also lie within or on the boundaries of a segment of a solubility parameter (SP) circle that defines the area on the graph that includes those solvents according to the invention that have sufficient polarity to produce the desired level of AKD selectivity, without being so polar that a high degree of mutual solubility with water reduces AKD purity by excessive moisture incursion, and to produce crystals that are large enough to be readily separated using mechanical techniques by and excludes the ones that do not meet those requirements. However, halogenated solvents such as chlorobenzene, dichlorobenzene, and trichloroethylene, which conform to the Hansen polar and hydrogen bonding solubility parameter scales within the defined segment of the SP circle but cause unacceptable health and environmental problems in conventional processes, are excluded from the solvents useable in the process according to the invention.

Using the standard equation of a circle, $(x-h)^2+(y-k)^2=r^2$, in which x and y are the coordinates of any point on the circle, and h and k are the coordinates of the center of the SP circle, a segment of which defines the area on the graph that includes the solvents according to one embodiment of the invention, has these values: polar solubility parameter, 6 MPa$^{1/2}$, and hydrogen bonding solubility parameter, 4 MPa$^{1/2}$. The circle radius is 3.5 MPa$^{1/2}$. The center therefore has 6 and 4 as its x, y coordinates. Substituting those values in the standard equation gives $(x-6)^2+(y-4)^2=3.5^2$, or $x^2+y^2-12x-8y+36+16=12.25$. (The equation is also satisfied, of course, if the square root of $(x-6)^2+(y-4)^2 \leq 3.5^2$). According to this embodiment of the invention, the acceptable oxygenated hydrocarbon solvents according to the invention have x, y coordinates such that $x^2+y^2-12x-8y+52 \leq 12.25$, provided that the Hansen polar solubility values of the acceptable oxygenated hydrocarbon solvents are greater than 2.75 MPa$^{1/2}$ and therefore in or on the margin of the SP circle that has 6 and 4 as its x, y coordinates or within or on the chord (at x=2.75) of the segment of the SP circle that lies to the left of the value of 2.75 on the y axis, which represents the chord of the segment of the circle that has 6 and 4 as its x, y coordinates.

In processes involving mechanical separation, solvents above and to the right of the SP circles tend to be so polar that moisture incursion during the dimerization reaction can be excessive, which results in low AKD assay. Solvents to the left of the circles (the chord of the segment in the second preferred embodiment) and below the circles are so non-polar that amine-hydrochloride precipitates are too small to be readily separated using mechanical techniques.

Taking 5 and 7 as random examples, $x^2+y^2-12.5x-8y+55.0625=10.5625$ and $x^2+y^2-12x-8y+52=10$, and thus is within each of the circles.

Preferred solvents have Hansen polar solubility parameter values in the range of 2.5 to 9.5 MPa$^{1/2}$ and Hansen hydrogen bonding parameter ($\delta_H$) values in the range of 0.5–7.5 MPa$^{1/2}$.

More preferably, oxygenated hydrocarbon solvents that conform to the Hansen polar and hydrogen bonding solubility parameter scales within the SP circle have a Hansen polar solubility parameter above 2.75 MPa$^{1/2}$, excluding the segment of the SP circle that lies to the left of x=2.75. Even more preferably, they have a Hansen polar solubility parameter between 2.75 MPa$^{1/2}$ and 9.25 MPa$^{1/2}$ and a Hansen hydrogen bonding parameter between 2 MPa$^{1/2}$ and 7.25 MPa$^{1/2}$. That area within the SP circle lies in the rectangle defined by the values x=2.75 and x=9.25 and y=2 and y=7.25. Most preferably, the selected solvents have polar solubility parameters between 6–7 MPa$^{1/2}$ and hydrogen bonding parameters between 3.5–5.5 MPa$^{1/2}$, or polar solubility parameters between 3.5–5.5 MPa$^{1/2}$ and hydrogen bonding parameters between 6–7 MPa$^{1/2}$.

Finally, a solvent must possess environmental neutrality and low health risks. For instance, aromatic hydrocarbons produce satisfactory high AKD assay and non-viscous alkyl ketene dimerization mixtures, but involve serious health and environmental concerns.

Solvents that meet the environmental and health criteria, possess the correct melting and boiling points, produce high assay alkyl ketene dimers, non-viscous alkyl ketene dimerization mixtures, and amine-hydrochloride precipitates amenable to mechanical separation can be classified as:

1. Esters; including ethyl acetate, propyl acetate, isopropyl acetate, butyl acetate, ethyl propionate, and methyl butyrate;
2. Ketones: including methyl ethyl ketone (MEK), methyl isobutyl ketone (MIBK), and cyclohexanone; and
3. The more polar ethers, such as anisole (methyl phenyl ether).

Useful solvents according to the invention can be mixed with environmentally neutral solvents that involve low health risks but are otherwise non-acceptable solvents to form dimerization solvent mixtures that when used in the reaction of fatty acid chloride and linear tertiary amines produces high AKD selectivity, large amine-hydrochloride crystals, and fluid dimerization mixtures.

Other chemical families contain solvents that fall within the circle but these solvents are unacceptable for the dimerization reaction. Aldehydes have the correct polarity balance but these solvents are unacceptable because they are not inert; i.e., they react with an ingredient of the reaction mixture, namely, the ketene intermediate. The halogenated hydrocarbon chemical family generally involve unacceptable environmental concerns.

Preferably, after the separation of amine-hydrochloride from the dimerization reaction mixture, the dimerization solvent is separated by distillation or solvent stripping, which results in the recovery of the alkyl ketene dimer product in a assay of at least 80%.

Also, according to the invention, alkyl ketene ketene dimer that contains the oxygenated hydrocarbon solvent is produced.

DETAILED DESCRIPTION OF THE INVENTION

The alkyl ketene dimers prepared in accordance with the present invention use $C_8$–$C_{32}$ fatty acids and fatty acid blends as starting materials.

Linear saturated fatty acids have the structure:

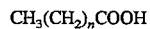

in which n=6–30, preferably 6 to 20. Suitable halides are conventionally derived from their corresponding carboxylic acids by halogenation, preferably chlorination. Chlorination with chlorinating reagents such as, phosphorus trichloride, phosphorus pentachloride, thionyl chloride, and phosgene.

According to the invention, long-chain carboxylic acid halides with 12 to 22 carbon atoms, or their mixtures, are preferred. Among the carboxylic acid halides, the carboxylic acid chlorides are the most suitable. Furthermore, mixtures of carboxylic acid chlorides of naturally occurring fatty acids are suitable for this process, e.g., fatty acids from tallow oil and palm oil. Particularly preferred is a mixture of palmitoyl chloride and stearyl chloride as the starting material.

The fatty acid chlorides can, if desired, be purified by known means such as vacuum distillation. They have the structure:

$$CH_3(CH_2)_nCOCl$$

in which n=6–30, preferably 6–20.

Linear tertiary amines are preferred for use in the invention. Linear tertiary amines suitable for use in the present invention are aprotic and preferably have low molecular weight. They include, for instance, trimethylamine, triethylamine, triisopropylamine, and tri-n-butylamine.

Particularly preferred linear tertiary amines have the formula:

$$\begin{array}{c} R_1 \\ | \\ N-R_2 \\ | \\ R_3 \end{array}$$

in which $R_1$, $R_2$, and $R_3$ are individually methyl, ethyl or n-propyl.

Linear tertiary amines having the preferred formula include trimethylamine, triethylamine, dimethylethylamine, methyldiethylamine, dimethyl-n-propylamine, etc. The most preferred tertiary amine is triethylamine (TEA).

In the preferred process of making alkyl ketene dimers according to the invention, the acid chloride and triethylamine are used in roughly equal molar proportions, preferably in exactly equimolar amounts or in a slight molar excess of the amine. An amine deficit at the end of the alkyl ketene dimerization reaction results in fatty acid chloride in the finished dimer that can be unacceptable in the ultimate alkyl ketene dimer application. A large molar excess of tertiary amine leaves a substantial amount of tertiary amine in the solvent after the physical separation of the amine hydrochloride. Residual amine in the alkyl ketene dimerization slurry complicates recovery of the solvent and can lead to hydrolysis of the alkyl ketene dimer product and lower alkyl ketene dimer assay.

The preferred mole ratio range of fatty acid chloride to tertiary amine is 1.0:1 to 1.0:1.1.

It is possible to add the fatty acid chloride to the tertiary amine in solution in the solvent, or to add the amine to the fatty acid chloride in solution, or simultaneously to add both fatty acid chloride and amine to the solvent. However, the preferred method is to add portions of the fatty acid chloride over a time interval to a stirred solution of the amine in the functional solvent.

In some cases, pre-addition of a small amount fatty acid chloride to a linear tertiary amine, preferably triethylamine, in the solvent will result in the formation of small seed aminehydrochloride crystals. As acid chloride addition is completed, the seed crystals grow to dimensions greater than the crystals obtained when no seeding is performed.

The preparation of the alkyl ketene dimers (AKD) of this invention by the reaction of the tertiary amine and the fatty acid halide is through a ketene intermediate (R=C=O); for instance, using triethylamine (TEA) and fatty acid chloride (RCOCl), the reaction is as follows:

Dehydrochlorination

Ketene Dimerization

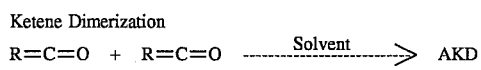

High purity solvents are preferably used in this invention to maximize product alkyl ketene dimer purity and assay. In particular, the solvent should be free of moisture and alcohols. Preferably, the moisture content of the solvent is no greater than 0.05% by weight and the alcohol content no greater than 0.3%.

Most preferably only the oxygenated hydrocarbon solvent of this invention is used (c.a., 99% or more by weight oxygenated hydrocarbon solvent). However, preferably at least about 30%, more preferably at least about 50%, even more preferably at least about 60%, of the solvent in an oxygenated hydrocarbon or mixture thereof.

Major considerations involved in the choice of the mass ratio of the fatty acid halide to the solvent are the solubility of the resulting dimer in the reaction mixture, the temperature of the reaction mixture and the cooling limitations of the particular reaction vessel employed. The greater the number or average number of carbon atoms in the chain of the fatty acid, the lower the solubility of the dimer in the solvent will be; dimers derived from behenic or $C_{22}$ fatty acid chloride have a lower solubility in solvent reaction mixture than dimers derived from fatty acid halides having fewer carbon atoms.

To prevent the simultaneous precipitation of tertiary amine hydrohalide and dimer in such cases, more solvent may be required to be included in the reaction mixture. Alternatively, a higher reaction mixture temperature may be employed to increase the solubility of the dimer product, especially just prior to the physical separation of the crystals of tertiary amine hydrohalide from the reaction mixture.

Because the dimerization reaction is completed at temperatures between 25° C. and 70° C., acceptable solvents must also have a melting point below 25° C. and boiling point above 70° C. In general, it is preferred to include in the reaction mixture solvent at least sufficient and preferably in excess of the amount necessary to maintain the alkyl ketene dimer in solution consistent with a maximum reaction mixture temperature of 70° C. and a preferred maximum reaction mixture temperature of 55° C.

Such preferred proportions are between about 30% and 1000% by mass of the solvent based upon the mass of the fatty acid halide or mixture of fatty acid halides. A particularly preferred concentration of the solvent is just above the concentration needed to avoid the precipitation of the alkyl ketene dimer at any point during the reaction cycle. In some circumstances it may be advantageous to add additional solvent during the course of the reaction to maintain the solubility of the alkyl ketene dimer as it is formed.

For the physical separation of the tertiary amine hydrohalide crystals from the continuous liquid phase of the reaction mixture, filtration such as vacuum filtration, filtration hastened by the use of centrifugal force, and even gravity filtration may be satisfactory. Particularly preferred methods of filtration are both rapid and limit moisture ingress. The choice of the filtration method having regard to the said considerations is conventional. Other physical methods of separation of the amine-hydrohalide can be used, such as permitting sedimentation of the hydrohalide and decanting off some or all of the alkyl ketene dimer containing reaction mixture. The sedimentation process could be assisted by centrifugation if required or convenient. In general, the amine-hydrohalide precipitates must have all linear dimensions greater than 5 microns to use mechanically assisted separation. The process of this invention is particularly suitable for processes involving centrifugation, or a combination of centrifugation and filtration.

After physical separation of the precipitated tertiary amine hydrohalide from the reaction mixture, the final stage of the process is the removal of solvent and any remaining tertiary amine from the alkyl ketene dimer. Conventional techniques for removing volatile substances from relatively non-volatile substances are appropriate, including distillation or vacuum distillation. Thin film evaporators are useful for small-scale operations. Preferably neither the alkyl ketene nor the solvent is exposed to moisture, and the solvent and other volatile reaction mixture components are recovered for re-use. Finally, the solvent should possess environmental neutrality and low health risks.

The following examples further illustrate the invention. The following fatty acids were used:
Pristerine 4916: a blend of fatty acids sold by Unichema International. It has the following approximate composition and physical properties:

| $C_{12-C14}$ saturated acids | 4% |
|---|---|
| $C_{16}$ saturated acids | 39% |
| $C_{18}$ saturated acid | 54% |
| $C_{20}$ saturated acid | 1% |
| $C_{18}$ unsaturated acids | 2% |
| Iodine value ($gI_2$/100 g) (max) | 2 |
| Titre °C. | 54–56 |
| Acid value (mg KOH/G) | 202–210 |
| Saponification value mg KOH/G | 204–212 |
| Unsaponifiable material % (max) | 1 |

Emersol E-132: a blend of fatty acids sold by Henkel/Emery Corporation. It has the following approximate composition and physical properties:

| $C_{14}$ saturated acids | 2.5% |
|---|---|
| $C_{15}$ saturated acids | 0.5% |
| $C_{16}$ saturated acids | 50% |
| $C_{17}$ saturated acid | 1.5% |
| $C_{18}$ saturated acid | 45.5% |
| Iodine value ($gI_2$/100 g) (max) | 0.5 |
| Titre °C. | 54.5–55.5 |
| Acid value (mg KOH/G) | 205–210 |
| Saponification value mg KOH/G | 205–210 |

EXAMPLE I

Preparation of an alkyl ketene dimer using methyl ethyl ketone ($\delta_p$=9.0, $\delta_H$=5.1) and methyl isobutyl ketone ($\delta_p$=6.1, $\delta_H$=4.1) as solvents:

Dry methyl ethyl ketone (2-butanone), 167 grams, was placed in a 500ml 3-necked flask equipped with nitrogen inlet, polytetrafluorethylene (PTFE) paddle stirrer condenser and dropping funnel. The apparatus was protected against moisture ingress. Dry nitrogen was bubbled through the methyl ethyl ketone for 30 minutes after which time the rate was reduced to a few bubbles per minute and dry triethylamine (41.3 g) was added with stirring. Fatty acid chloride (110 g) made from Pristerine 4916 fatty acid feedstock was then added dropwise with stirring over 30 minutes, the temperature being allowed to rise to 35° C. and being maintained at between 35° C. and 40° C. using a water bath. A slurry of triethylamine hydrochloride formed. The fluid reaction mixture was then stirred for a further 30 minutes and then heated to 45° C. when it was filtered by suction through a filter paper to separate the amine-hydrochloride which was washed with a small amount of 2-butanone. The filtrate containing the alkyl ketene dimer and excess triethylamine was then stripped of solvent under reduced pressure using a rotary evaporator and a water bath at 80° C. to give the alkyl ketene dimer. Analysis of the product showed it to have an alkyl ketene dimer assay of 83.3% and a non-volatile content of 99.8%.

Alkyl ketene dimer was made using methyl isobutyl ketone (4-methyl-2-pentanone) as the dimerization solvent and using the same conditions used for 2-butanone. Analysis of the product demonstrated an AKD assay of 91% and a non-volatile content of 99.8%.

EXAMPLE II

Preparation of an alkyl ketene dimer using methyl phenyl ether ($\delta_p$=4.1, $\delta_H$=6.8) as the solvent:

Dry methyl phenyl ether (anisole), 161 grams, and 2.1 grams of triethylamine were placed in a 500ml 5-necked flask equipped with nitrogen inlet, PTFE paddle stirrer condenser and dropping funnel. The anisole and triethylamine had been dehydrated by treatment with molecular sieves. The apparatus was protected against moisture ingress. The reaction vessel was at 45° C. Simultaneous addition of fatty acid chloride and triethylamine was begun. 95.6 grams of additional triethylamine was added to the reactor over a 5 minute period. 235.8 grams of fatty acid chloride was added over 75 minutes. The fatty acid chloride had been made from Emersol E-132 fatty acid feedstock using phosphorous trichloride. The reactor temperature was maintained at 45° C. using cooling water flowing through the glass reactor jacket. At the completion of acid chloride addition, the reactor was kept at 45° C. for fifty minutes with agitation. At the end of the hold period, the dimerization mixture was transferred to pint centrifuge tubes. The dimerization mixture was centrifuged to separate triethylamine-hydrochloride crystals. The recovered AKD/anisole solution was stripped in a 500-ml vessel under vacuum supplied by an aspirator at a temperature of 90° C. for three hours. Analysis of the product showed it to have an alkyl ketene dimer assay of 90%.

EXAMPLE III

Preparation of an alkyl ketene dimer using palmitoyl chloride, triethylamine, and solvents selected according to the invention, including less polar solvents:

The solvents selected according to the invention were isopropyl acetate ($\delta_p$=4.3, $\delta_H$=5.6), methyl phenyl ether (anisole, ($\delta_p$=4.1, $\delta_H$=6.8 ), butyl acetate ($\delta_p$=3.7, $\delta_H$=6.3 ), cyclohexanone ($\delta_p$=6.3, $\delta_H$=5.1), and tert-amyl methyl ether (TAME, $\delta_p$=6.1, $\delta_H$=3.9). 207.5 grams of each selected solvent and 85 grams triethylamine were placed into 500ml 5-necked flask equipped with nitrogen inlet, (PTFE) paddle stirrer condenser and dropping funnel. The selected solvent and triethylamine had been dehydrated by conventional treatment with molecular sieves. The apparatus was protected against moisture ingress. 207.5 grams of palmitoyl chloride was added over 50 minutes. The palmitoyl chloride (purchased from Aldrich) was greater than 98% pure. The reactor temperature was maintained at 45° C. using cooling water flowing through the glass reactor jacket. At the completion of acid chloride addition, the reactor was kept at 45° C. for fifty minutes with agitation. At the end of the hold period, the dimerization mixture was transferred to pint centrifuge tubes. The dimerization mixture was centrifuged to separate triethylamine-hydrochloride crystals. The recovered AKD/functional solvent was stripped in a 500-ml vessel under vacuum supplied by an aspirator at a temperature of 90° C. for three hours. Analysis of the product showed it to have an alkyl ketene dimer assay of between 80 and 92%. The results are reported in Table 1. They show that the experiments performed with the solvents selected according to the invention consistently produced AKD assays greater than 80% and frequently greater than 90%. The dimensions of the TEA-HCl crystals were measured using a microscope (only the two visible dimensions were measured). The selected solvents produced TEA-HCl crystals with linear dimensions greater than 5 micron.

TABLE I

A summary of the proportions of ingredients use in the above examples.

TABLE I

A summary of the proportions of ingredients use in the above examples.

| FORMULATION | SOLVENT | ACID CHLORIDE | AMINE |
|---|---|---|---|
| Example I | 167 parts | 110 parts | 44 parts |
| Example II | 165 parts | 240 parts | 96 parts |
| Example III | 210 parts | 210 parts | 88 parts |

EXAMPLE IV

A control preparation of alkyl ketene dimer using palmitoyl chloride, triethylamine, and dimerization solvents outside the scope of the invention.

Alkyl ketene dimer was formulated using the conditions in Example II but using low polarity aliphatic hydrocarbons outside the scope of the invention. The dimerization mixtures appeared more viscous. The recovered AKD consistently had assays less than 80% and triethylamine-hydrochloride crystals were small with at least one dimension being 5 microns or less. Similar experiments, performed with butyraldehyde, a reactable (not inert) solvent, outside the scope of the invention, also produced low assay AKD.

EXAMPLE V

Preparation of alkyl ketene dimer using palmitoyl chloride, triethylamine, and a mixture of solvents including 30% of a solvent selected according to the invention).

Experiments were performed under conditions similar to those of Example II except that the ratio of acid chloride to dimerization solvent was 0.69 grams palmitoyl chloride/1 milliliter of dimerization solvent and triethylamine was in 10% excess above the stoichiometric amount required for dehydrochlorination. In this case, a mixture by volume of 70% methyl cyclohexane ($\delta_P=0$, $\delta_H=1.0$) (MCH), an aliphatic solvent, and 30% methyl phenyl ether ($\delta_P=4.1$, $\delta_H=6.8$, according to the invention), was used as the dimerization solvent. Although the major part of the composition of the dimerization solvent was outside the scope of the invention, the dimerization in the presence of 30% of a solvent selected according to the invention produced amine-hydrochloride crystals that were easy to separate. After removal of the a triethylamine-hydrochloride crystals and the stripping of the dimerization solvent mixture and alkyl ketene dimer product of 89% purity was obtained.

TABLE II

Results of Examples I to IV

| Solvent | AKD Assay (wt %) | TEA-HCl Crystal Size (microns) |
|---|---|---|
| Preferred Solvents | | |
| isopropyl acetate | 91.2 | 10 × 10 |
| anisole (methyl phenyl ether) | 90.7 | 40 × 20 |
| butyl acetate | 89.7 | 30 × 10 |
| Acceptable Solvents | | |
| cyclohexanone | 86.0 | 20 × 60 |
| tert-amyl methyl ether (TAME) | 87.5 | 5 × 5 |
| Unaccetable Solvents | | |
| heptane | 65.8 | 5 × 10 |
| methyl cyclohexane | 75.3 | 5 × 10 |
| butyraldehyde | 62.0 | 100 × 30 |

Summary of Results in Table II

The solvents of the invention produced AKD assays above 80% and in some cases above 90%, and TEA-HCl crystals that were generally larger and easier to separate with a centrifuge. The dimerization slurries were not viscous. The solvents that are optimal for obtaining highest AKD assay with processes involving centrifugation are those with Hansen hydrogen bonding solubility parameter values between 6–7 $MPa^{1/2}$ and polar solubility parameters between 3.5–5.5 $MPa^{1/2}$ or solvents that have polar solubility parameters between 6–7 $MPa^{1/2}$ and hydrogen solubility parameters between 3.5–5.5 $MPa^{1/2}$. The optimal functional solvents that are in these ranges of solubility parameters are anisole, isopropyl acetate, and methyl isobutyl ketone (MIBK) and these solvents can be used to produce AKD of assays greater than 90%. Solvents within the range defined by the circle but outside the optimum range can be used to produce AKD with 80–87% AKD assay. When using less polar dimerization solvents AKD assay is generally less than 80%. When using non-polar dimerization solvents, dimerization slurries appear very viscous and amine-hydrochloride crystals can be difficult to separate.

EXAMPLE VI

Preparation of an alkyl dimer using anisole, triethylamine, and isostearoyl chloride, a branched fatty acid chloride made from Henkel/Emery Emersol-875* fatty acid feedstock using phosphorous trichloride.

*Emersol-857 is a product of Henkel/Emery corporation and is blend of fatty acids having the following approximate composition.

Dry methyl phenyl ether (anisole), 90 parts, was place in a 250 ml 5-necked flask equipped with nitrogen inlet, PTFE paddle stirrer, condenser, and dropping funnel. The apparatus was protected against moisture ingress. The reaction vessel was at 45° C. 22 parts of triethylamine was added into the reactor at once. 60 parts of isostearoyl chloride was added over 20 minutes. The reaction mixture was kept at 45° C. for total 2 hours. The triethylamine-hydrochloride salts were separated by suction filtration. The AKD/anisole solution was stripped under vacuum at 90° C. to recover the AKD. Analysis of the product showed it to have an alkyl ketene dimer assay of 88%.

| | |
|---|---|
| C$_{18}$ branched saturated acid | 70–76% |
| C$_{16}$ branched saturated acid | 6–7% |
| C$_{14}$ saturated acid | 7–11% |
| C$_{16}$ saturated acid | 4–5% |

EXAMPLE VI

Preparation of an alkyl dimer using anisole, triethylamine, and oleoyl chloride, an unsaturated fatty acid chloride made from Henkel/Emery Emersol-875* fatty acid feedstock using phosphorous trichloride.

*Emersol-857 is a product of Henkel/Emery corporation and is blend of fatty acids having the following approximate composition.

Alkyl Ketene Dimer was prepared from oleoyl chloride using triethylamine, anisole and following the same reaction procedure as that in the case 1 of Example III. The oleoyl chloride was made from Henkel/Emery Emersol 213 fatty acid feedstock using phosphorous trichloride. Analysis of the product showed it to have alkyl ketene dimer assay of 86–88%. *Emersol-213 is a product of Henkel/Emery corporation and is blend of fatty acids having the following approximate composition.

| | |
|---|---|
| C$_{18}$ unsaturated acids | 82% |
| C$_{16}$ unsaturated acid | 6% |
| C$_{14}$ unsaturated acid | 3% |
| C$_{14}$–C$_{17}$ saturated acids | 9% |

We claim:

1. A process for the synthesis of an alkyl ketene dimer by the dehydrohalogenation reaction of a C$_8$–C$_{32}$ aliphatic fatty acid halide with a ternary amine in a solvent wherein the tertiary amine hydrohalide is mechanically separated from the alkyl ketene dimer solvent solution and wherein the solvent comprises an oxygenated hydrocarbon solvent having a boiling point above 70° C. and Hansen polar and hydrogen bonding solubility values lying on or within a solubility parameter circle drawn on a parameter solubility map where the x-y axes are the Hansen polar and hydrogen bonding solubility parameter scales in MPa$^{1/2}$ units, respectively, the circle radius being 3.5 MPa$^{1/2}$, and the center of the circle the center having 6.25 and 4 and its x, y coordinates, the oxygenated hydrocarbon solvent having x, y coordinates such that $x^2+y^2-12.5x-8y+55.0625 \leq 12.25$.

2. A process for making an alkyl ketene dimer by the dehydrohalogenation reaction of a C$_8$–C$_{32}$ aliphatic fatty acid halide with a tertiary amine in a solvent wherein the tertiary amine hydrohalide is mechanically separated from the alkyl ketene dimer solvent solution and wherein the solvent comprises an oxygenated hydrocarbon solvent having a boiling point above 70° C. and Hansen polar and hydrogen bonding solubility values lying on or within the segment of a solubility parameter circle drawn on a parameter solubility map where the x-y axes are the Hansen polar and hydrogen bonding solubility parameter scales in MPa$^{1/2}$ units, respectively, the circle radius being 3.5 MPa$^{1/2}$, and the center of the circle having 6 and 4 as its x, y coordinates, the Hansen polar and hydrogen bonding solubility values of the oxygenated hydrocarbon solvents having x, y coordinates such that $x^2=y^2-12x-8y+52 \leq 12.25$, provided that the Hansen polar solubility value of the oxygenated hydrocarbon solvent is greater than 2.75 MPa$^{1/2}$.

3. A process for making an alkyl ketene dimer as claimed in claim 2, characterized in that the oxygenated hydrocarbon solvent has a Hansen polar solubility parameters in the range of 2.75–9.25 MPa$^{1/2}$ and Hansen hydrogen bonding solubility parameter values in the range of 2–7.5 MPa$^{1/2}$.

4. A process for making an alkyl ketene dimer, as claimed in claim 2, characterized in that the solvent has a melting point below 25° C.

5. A process for making an alkyl ketene dimer, as claimed in claim 3, characterized in that the solvent has a melting point below 25° C.

6. A process for making an alkyl ketene dimer, as claimed in claim 5, further characterized in that the solvent is selected from the group consisting of ketones, esters, and ethers.

7. A process for making an alkyl ketene dimer, as claimed in claim 2, further characterized in that the solvent is selected from the group consisting of methyl ethyl ketone, methyl isobutyl ketone, methyl phenyl ether, isopropyl acetate, butyl acetate, and cyclohexanone.

8. A process for making an alkyl ketene dimer, as claimed in claim 2, further characterized in that the dimer is produced in solution and crystals of tertiary amine hydrohalide are precipitated out of solution.

9. A process for making an alkyl ketene dimer, as claimed in claim 3, further characterized in that the dimer is produced in solution and crystals of tertiary amine hydrochloride are precipitated out of solution.

10. A process for making an alkyl ketene dimer, as claimed in claim 7, further characterized in that the dimer is produced in solution and crystals of tertiary amine hydrochloride are precipitated out of solution.

11. A process for making an alkyl ketene dimer as claimed in claim 8, further characterized in that the tertiary amine hydrohalide is separated from the alkyl ketene dimer solvent solution by filtration and the dimer is recovered by evaporation of the solvent.

12. A process for making an alkyl ketene dimer as claimed in claim 8, further characterized in that the tertiary amine hydrohalide is separated from the alkyl ketene dimer solvent solution by centrifugation and the dimer is recovered by evaporation of the solvent.

13. A process for making an alkyl ketene dimer as claimed in claim 9, further characterized in that the tertiary amine hydrochloride is separated from the alkyl ketene dimer solvent solution by filtration or centrifugation and the dimer is recovered by evaporation of the solvent.

14. A process for making an alkyl ketene dimer, as claimed in claim 10, further characterized in that the tertiary amine hydrochloride is separated from the alkyl ketene dimer solvent solution by filtration or centrifugation and the dimer is recovered by evaporation of the solvent.

15. A process for making an alkyl ketene dimer, as claimed in claim 2, characterized in that the dehydrohalogenation reaction is carried out with a saturated linear fatty acid.

16. A process for making an alkyl ketene dimer, as claimed in claim 3, characterized in that the dehydrohalogenation reaction is carried out with a saturated linear fatty acid.

17. A process for making an alkyl ketene dimer, as claimed in claim 5, characterized in that the dehydrohalogenation reaction is carried out with a saturated linear fatty acid.

18. A process for making an alkyl ketene dimer, as claimed in claim 14, characterized in that the dehydrohalogenation reaction is carried out with a saturated linear fatty acid.

19. A process for making an alkyl ketene dimer, as claimed in claim 15, characterized in that fatty acid halide is a chloride.

20. A process for making an alkyl ketene dimer, as claimed in claim 16, characterized in that fatty acid halide comprises palmitoyl chloride.

21. A process for making an alkyl ketene dimer, as claimed in claim 18, characterized in that fatty acid halide comprises palmitoyl chloride.

22. A process for making an alkyl ketene dimer, as claimed in claim 2, further characterized in that the amine is a linear tertiary amine selected from the group consisting of trimethylamine, triethyl-amine, dimethylethylamine, methyldiethylamine, and dimethyl-n-propylamine.

23. A process for making an alkyl ketene dimer, as claimed in claim 3, further characterized in that the amine is a linear tertiary amine selected from the group consisting of trimethylamine, triethyl-amine, dimethylethylamine, methyldiethyl-amine, and dimethyl-n-propylamine.

24. A process for making an alkyl ketene dimer, as claimed in claim 18, further characterized in that the amine is a linear tertiary amine selected from the group consisting of trimethylamine, triethyl-amine, dimethylethylamine, methyldiethyl-amine, and dimethyl-n-propylamine.

25. A process for making an alkyl ketene dimer, as claimed in claim 22, further characterized in that the linear tertiary amine is triethylamine.

26. A process for making an alkyl ketene dimer, as claimed in claim 23, further characterized in that the linear tertiary amine is triethylamine.

27. A process for making an alkyl ketene dimer, as claimed in claim 24, further characterized in that the linear tertiary amine is triethylamine.

28. A process for making an alkyl ketene dimer, as claimed in claim 15, further characterized in that the fatty acid halide is a chloride and the mole ratio of fatty acid chloride to tertiary amine is in the range 1.0:1 to 1.0:1.1.

29. A process for making an alkyl ketene dimer, as claimed in claim 20, further characterized in that the mole ratio of palmitoyl chloride to tertiary amine is in the range 1.0:1 to 1.0:1.1.

30. A process for making an alkyl ketene dimer, as claimed in claim 21, further characterized in that the mole ratio of palmitoyl chloride to tertiary amine is in the range 1.0:1 to 1.0:1.1.

31. A process for making an alkyl ketene dimer, as claimed in claim 22, further characterized in that the mole ratio of fatty acid halide to tertiary amine is in the range 1.0:1 to 1.0:1.1.

32. A process as claimed in claim 2, wherein the solvent comprises at least about 30% by weight of the oxygenated hydrocarbon solvent.

33. A process as claimed in claim 3, wherein the solvent comprises at least about 50% by weight of the oxygenated hydrocarbon solvent.

34. A process as claimed in claim 2, wherein the solvent comprises at least about 60% by weight of the oxygenated hydrocarbon solvent.

35. A process as claimed in claim 3, wherein the solvent comprises at least about 60% by weight of the oxygenated hydrocarbon solvent.

36. A process as claimed in claim 7, wherein the solvent comprises at least about 60% by weight of the oxygenated hydrocarbon solvent.

37. A process as claimed in claim 14, wherein the solvent comprises at least about 60% by weight of the oxygenated hydrocarbon solvent.

38. A process as claimed in claim 2, wherein the solvent comprises at least about 99% by weight of the oxygenated hydrocarbon solvent.

39. A process as claimed in claim 2, wherein the solvent comprises at least about 99% by weight of the oxygenated hydrocarbon solvent.

40. A process as claimed in claim 23, further characterized in that the mole ratio of fatty acid halide to tertiary amine is in the range 1.0:1 to 1.0:1.1.

41. A process for making an alkyl ketene dimer by the dehydrohalogenation reaction of a $C_8$–$C_{32}$ aliphatic fatty acid chloride with a tertiary amine in an inert solvent, the solvent comprising at least 30% of an oxygenated hydrocarbon or mixture of oxygenated hydrocarbons selected from the group consisting of esters other than ethyl acetate, ketones and aromatic ethers.

42. A process as claimed in claim 41 wherein the solvent has a melting point below 25° C. and a boiling point above 70° C.

43. A process for making an alkyl ketene dimer by the dehydrohalogenation reaction of a $C_8$–$C_{32}$ aliphatic fatty acid halide with a tertiary amine in a solvent comprising an oxygenated hydrocarbon solvent having a boiling point above 70° C. and wherein the Hansen polar solubility parameter is 6–7 $MPa^{1/2}$ and the Hansen hydrogen bonding parameter is 3.5–5.5 $MPa^{1/2}$ or the Hansen polar solubility parameter is 3.5–5.5 $MPa^{1/2}$ and the Hansen bonding parameter is 6–7 $MPa^{1/2}$.

44. A process for making an alkyl ketene dimer as claimed in claim 1, wherein the mechanical separation is selected from the group consisting of filtration, sedimentation, decantation and centrifugation.

45. A process for making an alkyl ketene dimer as claimed in claim 2, wherein the mechanical separation is selected from the group consisting of filtration, sedimentation, decantation, and centrifugation.

46. A process for making an alkyl ketene dimer as claimed in claim 3, wherein the mechanical separation is selected from the group consisting of filtration, sedimentation, decantation, and centrifugation.

47. A process for making an alkyl ketene dimer as claimed in claim 43, wherein the tertiary amine hydrohalide is mechanically separated from the alkyl ketene dimer solvent solution and the mechanical separation is selected from the group consisting of filtration, sedimentation, decantation, and centrifugation.

48. A process for making an alkyl ketene dimer as claimed in claim 1, wherein the mechanical separation is selected from the group consisting of centrifugation and a combination of centrifugation and filtration.

49. A process for making an alkyl ketene dimer as claimed in claim 3, wherein the mechanical separation is selected from the group consisting of centrifugation and a combination of centrifugation and filtration.

50. A process for making an alkyl ketene dimer as claimed in claim 46, wherein the hydrocarbon solvent has a melting point below 25° C. and is selected from the group consisting of ketones, esters, and ethers.

51. A process for making an alkyl ketene dimer as claimed in claim 1, wherein the hydrocarbon solvent is selected from the group consisting of methyl ethyl ketone, methyl isobutyl ketone, methyl phenyl ether, isopropyl acetate, butyl acetate, and cyclohexanone.

52. The process of claim 43 wherein solvent has a melting point below 25° C. and the Hansen polar solubility parameter is 6–7 $MPa^{1/2}$ and the Hansen hydrogen bonding parameter is 3.5–5.5 $MPa^{1/2}$.

53. The process of claim 43 wherein the solvent has a melting point below 25° C. and the Hansen polar solubility parameter is 3.5–5.5 $MPa^{1/2}$ and the Hansen bonding parameter is 6–7 $MPa^{1/2}$.

54. A process for the synthesis of an alkyl ketene dimer by the dehydrohalogenation reaction of a $C_8$–$C_{32}$ aliphatic fatty acid halide with a tertiary amine in a solvent comprising an oxygenated hydrocarbon solvent selected from the group consisting of ketones, esters other than ethyl acetate, and ethers having a boiling point above 70° C. and, Hansen polar and hydrogen bonding solubility values lying on or within a solubility parameter circle drawn on a parameter solubility map where the x-y axes are the Hansen polar and hydrogen bonding solubility parameter scales in $MPa^{1/2}$ units, respectively, the circle radius being 3.5 $MPa^{1/2}$, and the center of the circle the center having 6.25 and 4 as its x, y coordinates, the oxygenated hydrocarbon solvent having x, y coordinates such that $x^2+y^2-12.5x-8y+55.0625 \leq 12.25$.

55. The process of claim 54 wherein the solvent it a ketone.

56. The process of claim 54 wherein the solvent it an ether.

57. A process for making an alkyl ketene dimer by the dehydrohalogenation reaction of a $c_8$–$C_{32}$ aliphatic fatty acid halide with a tertiary amine in a solvent comprising an oxygenated hydrocarbon solvent selected from the group consisting of ketones, esters other than ethyl acetate, and ethers having a boiling point above 70° C. and Hansen polar and hydrogen bonding solubility values lying on or within the segment of a solubility parameter circle drawn on a parameter solubility map where the x-y axes are the Hansen polar and hydrogen bonding solubility parameter scales in $MPa^{1/2}$ units, respectively, the circle radius being 3.5 $MPa^{1/2}$, and the center of the circle having 6 and 4 as its x, y coordinates, the Hansen polar and hydrogen bonding solubility values of the oxygenated hydrocarbon solvents having x, y coordinates such that $x^2+y^2-12x-8y+52 \leq 12.25$, provided that the Hansen polar solubility value of the oxygenated hydrocarbon solvent is greater than 2.75 $MPa^{1/2}$.

58. The process of claim 57 wherein the solvent it a ketone.

59. The process of claim 57 wherein the solvent it an ether.

60. The process of claim 54 wherein the solvent is an ester selected from the group consisting of propyl acetate, isopropyl acetate, butyl acetate, ethyl propionate, and methyl butyrate.

61. The process of claim 54 wherein the solvent is selected from the group consisting of methyl ethyl ketone, methyl isobutyl ketone, and cyclohexanone and anisole.

* * * * *